(12) United States Patent
Ishii et al.

(10) Patent No.: US 11,756,673 B2
(45) Date of Patent: Sep. 12, 2023

(54) MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventors: Hideaki Ishii, Nasushiobara (JP); Shigeo Kaminaga, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 135 days.

(21) Appl. No.: 16/843,961

(22) Filed: Apr. 9, 2020

(65) Prior Publication Data
US 2020/0327979 A1    Oct. 15, 2020

(30) Foreign Application Priority Data

Apr. 10, 2019  (JP) ................. 2019-075111

(51) Int. Cl.
| | |
|---|---|
| G06K 9/00 | (2022.01) |
| G16H 30/40 | (2018.01) |
| G06T 7/00 | (2017.01) |
| G16H 15/00 | (2018.01) |
| G16H 50/20 | (2018.01) |

(52) U.S. Cl.
CPC .......... G16H 30/40 (2018.01); G06T 7/0014 (2013.01); G16H 15/00 (2018.01); G16H 50/20 (2018.01)

(58) Field of Classification Search
CPC ...... G06T 7/0014; G16H 15/00; G16H 30/40; G16H 50/20
See application file for complete search history.

(56) References Cited

U.S. PATENT DOCUMENTS

| | | | |
|---|---|---|---|
| 2012/0176408 A1 | 7/2012 | Moriya | |
| 2013/0174077 A1* | 7/2013 | Asami | A61B 5/7435 |
| | | | 715/771 |

(Continued)

FOREIGN PATENT DOCUMENTS

| | | |
|---|---|---|
| JP | H09-167188 A | 6/1997 |
| JP | 2002-022748 A | 1/2002 |

(Continued)

OTHER PUBLICATIONS

Office Action dated Apr. 4, 2023 in Japanese Application No. 2019-075111.

(Continued)

*Primary Examiner* — Xin Jia
(74) *Attorney, Agent, or Firm* — Oblon, McClelland, Maier & Neustadt, L.L.P.

(57) ABSTRACT

A medical information processing apparatus of an embodiment includes processing circuitry. The processing circuitry acquires a plurality of pieces of output data respectively output from a plurality of analysis processes to which medical image data is input as input data. The processing circuitry selectively extracts, from the pieces of output data, a plurality of pieces of output data based on an extraction condition. The processing circuitry performs control to display a plurality of pieces of information corresponding to the pieces of extracted output data and a medical image related to any one piece of the information and generated from the medical image data.

13 Claims, 11 Drawing Sheets

(56) References Cited

U.S. PATENT DOCUMENTS

| | | | |
|---|---|---|---|
| 2014/0088993 A1 | 3/2014 | Itoh et al. | |
| 2015/0269315 A1 | 9/2015 | Arakita et al. | |
| 2015/0363053 A1* | 12/2015 | Aoyama | H04N 21/4725 |
| | | | 715/838 |
| 2016/0093045 A1* | 3/2016 | Koyasu | G16H 30/40 |
| | | | 382/128 |
| 2016/0300351 A1* | 10/2016 | Gazit | G06T 7/187 |
| 2019/0057504 A1* | 2/2019 | Kobayashi | G06V 10/764 |
| 2020/0161005 A1* | 5/2020 | Lyman | G06K 9/6262 |

FOREIGN PATENT DOCUMENTS

| | | |
|---|---|---|
| JP | 2004-357866 A | 12/2004 |
| JP | 2010-167144 A | 8/2010 |
| JP | 2011-086276 A | 4/2011 |
| JP | 2013-228800 A | 11/2013 |
| JP | 2014-067344 A | 4/2014 |
| JP | 2014-142925 A | 8/2014 |
| JP | 6483890 B1 | 3/2019 |

OTHER PUBLICATIONS

Chinese Notification of Rejection dated May 11, 2023 in Chinese Patent Application No. 202010272632.9, therein, 10 total pages.

\* cited by examiner

FIG.2

| WORK LIST | | | | |
|---|---|---|---|---|
| No. | STATUS | RECEPTION TIME | RECEPTION NUMBER | PATIENT ID |
| 1 | COMPLETED (2) | | | |
| 2 | COMPLETED | | | |
| 3 | COMPLETED (1) | | | |
| 4 | NOT YET | | | |
| 5 | NOT YET | | | |
| 6 | NOT YET | | | |
| 7 | NOT YET | | | |
| 8 | NOT YET | | | |
| 9 | NOT YET | | | |
| 10 | NOT YET | | | |
| ... | NOT YET | | | |

FIG.4A

▼ DISEASE: XXXX

ALGORITHM A

1
| | |
|---|---|
| Region | LCx |
| Lesion | 2 |
| Agatston | 136.63 |
| Volume | 102.47 |
| Mean | 297.79 |
| SD | 641.38 |

✓ Accepted     ✗ Ignore

ALGORITHM B

2
| | |
|---|---|
| Volume | 231.6mm |
| Mean D. | 9.3mm |
| Max D. | 10.2mm |
| Short Axis D. | 8.5mm |
| Min/Max | -815/39HU |
| Avg | -464HU |

✓ Accept     ✗ Ignore

3
| | |
|---|---|
| Volume | 231.6mm |
| Mean D. | 9.3mm |
| Max D. | 10.2mm |
| Short Axis D. | 8.5mm |
| Min/Max | -815/39HU |
| Avg | -464HU |

✓ Accept     ✗ Ignore

ALGORITHM D

4
.........   ......
.........   ......
.........   ......
.........   ......
.........   ......
.........

✓ Accepted     ✗ Ignore

| ▼ DISEASE: XXXX |
|---|

ALGORITHM A

1
Region LCx
Lesion 2
Agatston 136.63
Volume 102.47
Mean 297.79
SD 641.38

[ ✓ Accepted ]  [ ✕ Ignore ]

ALGORITHM C

2
Min D. 65.77mm
Max D. 73.65mm
Max/Area 3402.32mm
Volume 248.05mm

[ ✓ Accept ]  [ ✕ Ignore ]

~R2

ALGORITHM E

3
.........  ......
.........  ......
.........  ......
.........  ......
.........  ......
.........  ......
.........  ......

[ ✓ Accept ]  [ ✕ Ignore ]

FIG.8

| No. | STATUS | RECEPTION TIME | RECEPTION NUMBER | PATIENT ID |
|---|---|---|---|---|
| 1 | COMPLETED (2) | | | |
| 2 | COMPLETED | | | |
| 3 | COMPLETED (1) | | | |
| 4 | COMPLETED (3) | | | |
| 5 | NOT YET | | | |
| 6 | NOT YET | | | |
| 7 | NOT YET | | | |
| 8 | NOT YET | | | |
| 9 | NOT YET | | | |
| 10 | NOT YET | | | |
| ... | NOT YET | | | |

WORK LIST

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2019-75111, filed on Apr. 10, 2019; the entire contents of which are incorporated herein by reference.

FIELD

Embodiments described herein relate generally to a medical information processing apparatus and a medical information processing method.

BACKGROUND

In the related art, a technology of performing an analysis process on medical image data and using an analysis result for diagnosis support has been used. For example, in recent years, artificial intelligence (AI) has been used for diagnosis support of medical image data collected by a medical image diagnostic apparatus. As an example, a detection process of a lesion candidate included in the medical image data is performed using a learned model generated by machine learning using learning data. A doctor can use a result of the detection process to prevent a lesion candidate from being overlooked.

BRIEF DESCRIPTION OF THE DRAWINGS

FIG. 2 is a diagram illustrating an example of a work list according to a first embodiment;

FIG. 4A is a diagram illustrating an example of a group of analysis results according to the first embodiment;

FIG. 4B is a diagram illustrating an example of a group of analysis results according to the first embodiment;

FIG. 8 is a diagram for explaining the processing of a control function according to the first embodiment.

DETAILED DESCRIPTION

According to an embodiment, a medical information processing apparatus of an embodiment includes processing circuitry. The processing circuitry is configured to acquire a plurality of pieces of output data respectively output from a plurality of analysis processes to which medical image data is input as input data. The processing circuitry is configured to electively extract, from the pieces of output data, a plurality of pieces of output data based on an extraction condition. The processing circuitry is configured to perform control to display a plurality of pieces of information corresponding to the pieces of extracted output data and a medical image related to any one piece of the information and generated from the medical image data.

Hereinafter, with reference to the drawings, an embodiment of a medical information processing apparatus and a medical information processing method will be described in detail. Note that the medical information processing apparatus and the medical information processing method according to the present application are not limited to the following embodiments. Furthermore, the embodiment can be combined with other embodiments or the related art as long as there is no contradiction in processing content.

First Embodiment

Figure 1:
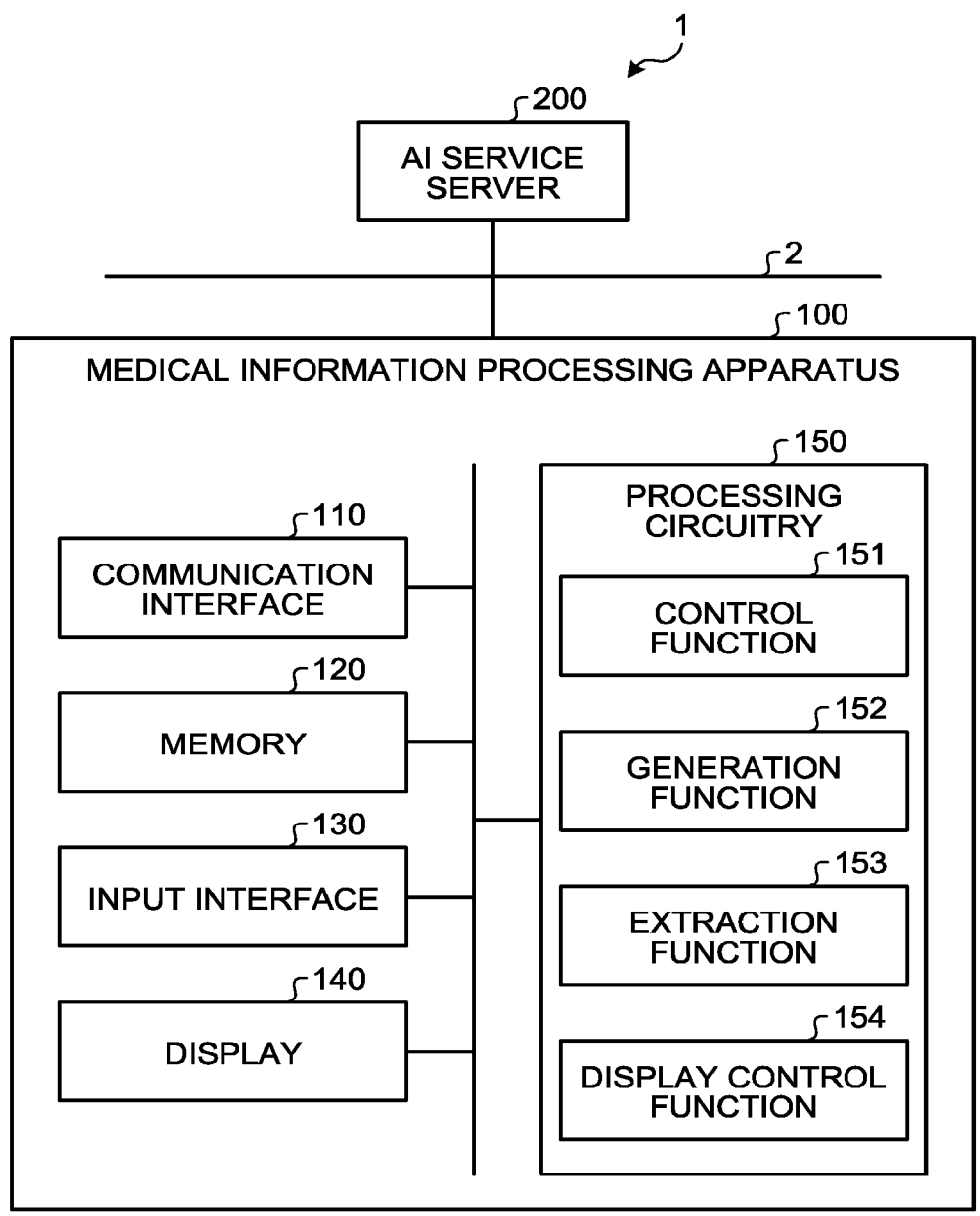
FIG. 1 is a diagram illustrating an example of a configuration of a medical information processing apparatus according to an embodiment.

Hereinafter, a first embodiment of the present application will be described. Note that, in the first embodiment, a case where an artificial intelligence (AI)-based process is used as an analysis process to be used for diagnosis support will be described. FIG. 1 is a diagram illustrating an example of a configuration of a medical information processing apparatus 100 according to the present embodiment. As illustrated in FIG. 1, the medical information processing apparatus 100 according to the present embodiment is included in a medical information processing system 1 and is communicably connected to, for example, an AI service server 200 via a network 2.

The AI service server 200 is a server device that provides an application programming interface (API) for an algorithm for machine learning or deep learning. Specifically, the AI service server 200 receives learning data including input data and teacher data based on the input data via the network 2, and generates a learned model by machine learning using the received learning data. Then, the AI service server 200 inputs the input data to the generated learned model, thereby outputting output data based on the learned model.

The AI service server 200 according to the present embodiment has various learned models and provides APIs for various image processing algorithms. For example, the AI service server 200 provides APIs for various algorithms for various organs such as the brain, lungs, heart, and liver, and for an algorithm for outputting various results for each organ. As an example, the AI service server 200 provides APIs for an algorithm for detecting a characteristic region from a difference in luminance values in medical image data, an algorithm for detecting a region indicating a characteristic perfusion state from a perfusion image, an algorithm for detecting a region indicating a characteristic shape in the shape of a blood vessel, and the like, for the brain.

Furthermore, the AI service server 200 can provide APIs for various image processing algorithms for medical image data collected by various modalities of an X-ray diagnostic apparatus, an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, and the like. That is, the AI service server 200 can include a plurality of learned models that use each medical image data collected by the aforementioned various modalities as input data.

Furthermore, the AI service server 200 can include a plurality of learned models using the same medical image data as input data. That is, the AI service server 200 can also output different output data by inputting the same medical image data to different learned models.

For example, the AI service server 200 acquires a plurality of pieces of learning data (original image and teacher data) with reference to a DB. Then, the AI service server 200 inputs the acquired original image and teacher data to its own machine learning engine and performs machine learning. The AI service server 200 performs the machine learning on various learning data and generates various learned models.

The machine learning engine compares, for example, an image feature amount of the input original image with an image feature amount in the teacher data, thereby determining an optimal parameter. For example, the machine learning engine determines the optimal parameter by using various algorithms such as deep learning, neural network, logistic regression analysis, non-linear discriminant analysis, support vector machine (SVM), random forest, and Naive Bayes.

As a result of such machine learning, the AI service server 200 generates a plurality of learned models that output various image processing results based on the original image. Then, the AI service server 200 stores the generated learned models in own memory. Note that, at this time, when previously generated learned models have already been stored in the memory, the AI service server 200 can replace the stored learned models with the newly generated learned models.

Furthermore, for example, during operation, the AI service server 200 receives medical image data from the medical information processing apparatus 100 and inputs the received medical image data to an applicable learned model, thereby outputting various image processing results. Then, the AI service server 200 transmits the output various image processing results to the medical information processing apparatus 100.

The medical information processing apparatus 100 acquires medical image data collected by a medical image diagnostic apparatus and transmits the acquired medical image data to the AI service server 200. Furthermore, the medical information processing apparatus 100 acquires output information of the learned model from the AI service server 200. For example, the medical information processing apparatus 100 is implemented by a computer device such as a server, a workstation, a personal computer, and a tablet terminal.

Although FIG. 1 illustrates a case where the medical information processing apparatus 100 directly transmits/receives the medial image data and the output information to/from the AI service server 200, the embodiment is not limited thereto and, for example, a device configured to relay data may be provided between the medical information processing apparatus 100 and the AI service server 200. In such a case, for example, a server device storing therein the medial image data is connected between the medical information processing apparatus 100 and the AI service server 200, and transmits/receives the medial image data and the output information to/from the medical information processing apparatus 100 and to/from the AI service server 200.

As illustrated in FIG. 1, the medical information processing apparatus 100 includes a communication interface 110, a memory 120, an input interface 130, a display 140, and processing circuitry 150, and is operated by a radiologist or a doctor in charge who interprets medical images.

The communication interface 110 is connected to the processing circuitry 150 and controls communication performed between the medical information processing apparatus 100 and the AI service server 200. Specifically, the communication interface 110 receives various output information from the AI service server 200 and outputs the received information to the processing circuitry 150. For example, the communication interface 110 is implemented by a network card, a network adapter, a network interface controller (NIC), and the like.

The memory 120 is connected to the processing circuitry 150 and stores therein various data. For example, the memory 120 stores therein the medical image data collected by the medical image diagnostic apparatus, the output information acquired from the AI service server 200, and the like. Furthermore, the memory 120 stores therein various computer programs for performing various functions by being read and executed by the processing circuitry 150. For example, the memory 120 is implemented by a semiconductor memory device such as a random-access memory (RAM) and a flash memory, a hard disk, and an optical disc.

The input interface 130 is connected to the processing circuitry 150 and receives various instructions and information input operations from an operator. Specifically, the input interface 130 converts the input operation received from the operator into an electrical signal and outputs the electrical signal to the processing circuitry 150. For example, the input interface 130 is implemented by a trackball, a switch button, a mouse, a keyboard, a touchpad for performing an input operation by touching an operation surface, a touch screen in which a display screen and a touch pad are integrated, a non-contact input circuit using an optical sensor, a voice input circuit, and the like. Note that, in the present specification, the input interface 130 is not limited to one including physical operation parts such as a mouse and a keyboard. For example, an example of the input interface 130 also includes an electrical signal processing circuit that receives an electrical signal corresponding to an input operation from an external input device provided separately from the apparatus, and outputs the electrical signal to a control circuit. The input interface 130 is an example of a receiving unit.

The display 140 is connected to the processing circuitry 150 and displays various information and images. Specifically, the display 140 converts information and image data sent from the processing circuitry 150 into an electrical signal for display and outputs the electrical signal for display. For example, the display 140 is implemented by a liquid crystal monitor, a cathode-ray tube (CRT) monitor, a touch panel, and the like.

The processing circuitry 150 controls the operation of the medical information processing apparatus 100 according to the input operation received from the operator via the input interface 130. For example, the processing circuitry 150 is implemented by a processor.

So far, the configuration of the medical information processing apparatus 100 according to the present embodiment has been described. With such a configuration, the medical information processing apparatus 100 can improve the usefulness in diagnosis support.

As described above, in recent years, the AI has been used for diagnosis support of medical image data. Furthermore, in recent years, as the type of AI-based image processing increases, various algorithms can be applied to medical image data to obtain various analysis results. Such AI-based diagnosis support can be used to prevent a lesion candidate from being overlooked by obtaining various analysis results before interpretation of a radiologist.

However, as the analysis results obtained by the AI increase, analysis results confirmed by a doctor such as a radiologist increase, resulting in an increase in the burden on the doctor. In this regard, in the present embodiment, the analysis results obtained by the AI are displayed in a form that is easier to confirm, thereby improving the usefulness in AI diagnosis support. Specifically, when displaying analysis results received from the AI service server 200, the medical information processing apparatus 100 groups and displays the results based on an extraction condition, thereby providing a display form in which the analysis results are more easily confirmed.

Hereinafter, details of the medical information processing apparatus 100 according to the present embodiment will be described. As illustrated in FIG. 1, the processing circuitry 150 of the medical information processing apparatus 100 performs a control function 151, a generation function 152, an extraction function 153, and a display control function 154. The control function 151 is an example of an acquisition unit and a control unit. Furthermore, the extraction function 153 is an example of an extraction unit. Furthermore, the display control function 154 is an example of a display control unit.

The control function 151 performs control to perform processing according to various requests input via the input interface 130. For example, the control function 151 controls the transmission/reception of medical image data and the like and the storage of the medical image data in the memory 120 via the communication interface 110. Furthermore, for example, the control function 151 controls the reception of the output information of the AI service server 200 and the storage of the output information in the memory 120 via the communication interface 110.

For example, the control function 151 acquires medial image data from the medical image diagnostic apparatus, a medical image storage apparatus, and the like according to a medial image data acquisition request input via the input interface 130, and stores the acquired medial image data in the memory 120. Then, the control function 151 transmits the medial image data stored in the memory 120 to the AI service server 200 according to a medial image data transmission request input via the input interface 130. Moreover, the control function 151 receives the output information from the AI service server 200 and stores the output information in the memory 120. The transmission/reception of the medial image data and the reception of the output information are performed for each subject (patient ID), and each piece of information is stored in the memory 120 in correlation with the patient ID. Furthermore, for example, the control function 151 performs various processes according to an operation performed by the operator on the output information of the AI service server 200. These processes will be described in detail later.

The generation function 152 performs various types of image processing on the medical image data, thereby generating various medical images for display. Specifically, the generation function 152 performs image processing on the medical image data, thereby generating various morphological images indicating the morphological information of parts and various functional images including the functional information of parts. For example, the generation function 152 generates morphological images such as a volume rendering image, a surface rendering image, a curved multiplanar reconstruction (CPR) image, a multiplanar reconstruction (MPR) image, a stretched multiplanar reconstruction (SPR) image, a Slab maximum intensity projection (MIP) image, a virtual endoscope image, and a developed image, and functional images such as a perfusion image, a PET image, a SPECT image, and a medical image including a result of functional analysis of other parts. Note that the aforementioned example is merely an example and the generation function 152 can generate various other morphological images and functional images according to the collected medical image data.

For example, the generation function 152 generates a medical image related to the analysis result of the AI service server 200. For example, the generation function 152 generates a medical image indicating the position of the analysis result. As an example, the generation function 152 generates a medical image indicating a lesion candidate region detected by the AI service server 200.

The extraction function 153 selectively extracts a plurality of pieces of output data from the pieces of output data based on the extraction condition. Specifically, the extraction function 153 classifies analysis results, which are output by a plurality of analysis processes, based on the extraction condition. For example, the extraction function 153 groups a plurality of pieces of output data, which is output from the learned models in the AI service server 200, based on the extraction condition. The process of the extraction function 153 will be described in detail later.

The display control function 154 performs control to display a plurality of pieces of information corresponding to the pieces of output data extracted by the extraction function 153 and a medical image related to any one piece of the information and generated from the medical image data. Specifically, the display control function 154 allows an analysis result corresponding to the pieces of output data grouped by the extraction function 153 to be displayed in parallel with a corresponding medical image. The process of the display control function 154 will be described in detail later.

As described above, in the medical information processing apparatus 100, output information is stored for each subject. An operator (a radiologist, a doctor in charge, and the like) who operates the medical information processing apparatus 100 observes medical image data of each subject and makes a diagnosis. That is, the operator operates the input interface 130 to display medical images of each subject on the display 140, and observes the medical images.

In the medical information processing apparatus 100, for example, a work list as illustrated in FIG. 2 can be used to select a subject to be diagnosed. FIG. 2 is a diagram illustrating an example of the work list according to the first embodiment. For example, the display control function 154 allows the work list illustrated in FIG. 2 to be displayed on the display 140 when an operation for starting diagnosis (interpretation) is performed. For example, as illustrated in FIG. 2, the work list includes "No.", "Status", "Reception time", "Reception number", and "Patient ID".

Here, "No." in FIG. 2 indicates the order in which diagnosis (interpretation) is performed, and for example, is assigned according to the order of reception, the order of an emergency, and the like. Furthermore, "Status" in FIG. 2 indicates the current state of each subject in image diagnosis. Although FIG. 2 illustrates only "Completed" indicating a state where the image diagnosis has been completed and "Not yet" indicating a state where the image diagnosis has not been completed, the work list may include a status indicating a state of waiting for results from the AI service server 200. Furthermore, the number in parentheses next to "Completed" in the status indicates the number that the operator has approved the analysis results of the AI service server 200, which will be described in detail later.

Furthermore, "Reception time" in FIG. 2 indicates a date and time when the image diagnosis was ordered. Furthermore, "Reception number" in FIG. 2 is a number assigned when the image diagnosis was ordered, and is a number for specifying each subject among a plurality of subjects for which the image diagnosis was ordered. Furthermore, "Patient ID" in FIG. 2 is an identifier for uniquely specifying each subject in a hospital.

For example, the operator refers to the work list illustrated in FIG. 2 and selects a subject to be diagnosed (interpreted) next. As an example, the operator refers to the work list illustrated in FIG. 2 and selects the subject of "No. 4" whose status is "Not yet" via the input interface 130. In response to this operation, the display control function 154 allows the display 140 to display a medical image to be interpreted.

In the medical information processing apparatus 100 according to the present embodiment, the display control function 154 allows the analysis results received from the AI service server 200 to be displayed in parallel with a medical image of a subject. As described above, in the medical information processing apparatus 100, when the analysis results received from the AI service server 200 are displayed, the results are grouped and displayed based on the extraction condition.

For example, the extraction function 153 uses the type of the analysis processes as the extraction condition and extracts output data for each type of the analysis processes. As an example, the extraction function 153 uses the type of the learned models (algorithms) as the extraction condition and extracts output data for each type of the learned models. The display control function 154 performs control to display a plurality of pieces of information corresponding to a plurality of pieces of output data for each type of the learned models. That is, the display control function 154 collectively collects the analysis results of the AI service server 200 for each algorithm and allows the analysis results to be displayed in correlation with corresponding medical images.

Figure 3:
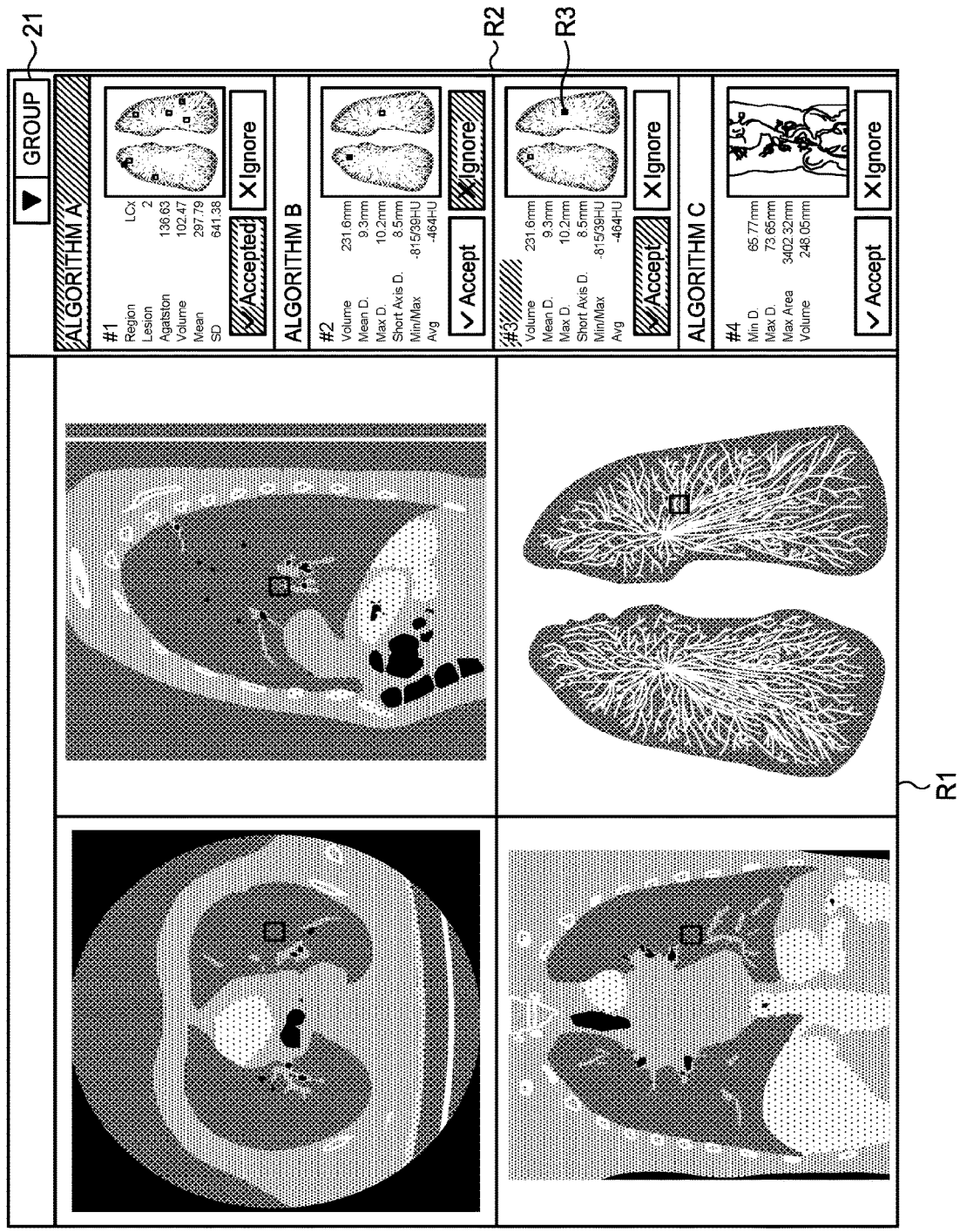
FIG. 3 is a diagram illustrating an example of display by a display control function according to the first embodiment.

FIG. 3 is a diagram illustrating an example of display by the display control function 154 according to the first embodiment. For example, as illustrated in FIG. 3, the display control function 154 allows the medial images and the analysis results received from the AI service server 200 to be simultaneously displayed on a display screen having a display region R1 for displaying the medial images and a display region R2 for displaying the analysis results. As indicated in the display region R2 of FIG. 3, for example, the display control function 154 allows the analysis results of algorithms A to C to be displayed. That is, the display control function 154 allows the analysis results of the algorithms A to C extracted by the extraction function 153 to be displayed in the display region R2.

The analysis result includes, for example, a thumbnail image on which the output result of the analysis process has been reflected and analysis information on the output result. For example, the analysis result includes a thumbnail image indicating the position of a detection result detected in the analysis process and analysis information. As an example, as illustrated in FIG. 3, the analysis result includes a thumbnail image indicating the position of a lesion candidate region detected by the learned model and analysis information on the size and the like of the lesion candidate region. For example, the analysis information of the algorithm A includes a thumbnail image indicating the positions (square positions on the thumbnail image) of seven lesion candidate regions detected by the algorithm A. Although FIG. 3 illustrates regions detected by the algorithms, when points are detected by the algorithms, the points are indicated at the detected positions on the thumbnail image. Furthermore, although FIG. 3 illustrates squares as marks indicating positions, the embodiment is not limited thereto and other shapes or actually detected shapes may be used.

The operator can designate a plurality of analysis results (for example, respective lesion candidate regions) via the input interface 130. For example, when the lesion candidate region is designated by the operator, as indicated in the thumbnail image in FIG. 3, the display control function 154 allows the inside of the square at the position of the designated lesion candidate region to be painted and highlighted for display. Then, the display control function 154 allows analysis information such as the volume, the length of a long axis, the length of a short axis, and the like of the designated lesion candidate region to be displayed next to the thumbnail. Moreover, the display control function 154 allows a medical image related to the designated lesion candidate region to be displayed in the display region R1.

Similarly for the algorithms B and C extracted by the extraction function 153, the display control function 154 allows analysis results including a thumbnail image indicating the position of a lesion candidate region by the learned model and analysis information such as the size and the like of the lesion candidate region to be displayed. For example, as illustrated in FIG. 3, the display control function 154 allows two analysis results of the algorithm B and an analysis result of the algorithm C to be displayed on the display screen.

As described above, the analysis results are grouped and displayed, so that the operator can easily grasp what kind of analysis results are present and can efficiently confirm the analysis results. For example, the operator designates the position of the lesion candidate region included in the analysis result of each algorithm and determines whether to approve the analysis result while observing the image. For example, when approving the analysis result, the operator presses an "Accept" button via the input interface 130, and when not approving the analysis result, the operator presses an "Ignore" button via the input interface 130.

As an example, the operator designates a lesion candidate region R3 in the second thumbnail of the algorithm B. Accordingly, the display control function 154 allows analysis information including the volume and the like of the lesion candidate region R3 to be displayed in the display region. At the same time, the display control function 154 allows the medial images generated by the generation function 152 and corresponding to the lesion candidate region R3 to be displayed in the display region R1. In FIG. 3, for example, the display control function 154 allows an MPR image of an axial section (upper left), a sagittal section (upper right), and a coronal section (lower left) including the lesion candidate region R3, and a volume rendering image (lower right) to be displayed in the display region R1. Furthermore, the display control function 154 allows marks (for example, squares) to be displayed at positions corresponding to the lesion candidate region R3 in the MPR image of the axial section, the sagittal section, and the coronal section and the volume rendering image.

The operator observes the analysis information of the lesion candidate region R3 displayed in the display region R2 and each medical image displayed in the display region R1, determines whether the lesion candidate region R3 is a lesion, and presses the "Accept" button or the "Ignore" button. In such a case, the control function 151 allows whether the operator has approved (whether the "Accept"

button has been pressed or the "Ignore" button has been pressed) to be stored in correlation with the lesion candidate region R3. That is, the control function 151 allows information regarding whether approval has been given to the second analysis result of the algorithm B stored in the memory 120 to be stored in correlation with the lesion candidate region R3.

Note that the operator can designate a plurality of lesion candidate regions. For example, the operator designates two lesion candidate regions indicated in the thumbnail image of the second analysis result of the algorithm B. In such a case, when the designated lesion candidate regions are depicted in the medical image in the display region R1, the display control function 154 allows marks indicating the positions of the lesion candidate regions to be displayed. For example, when the designated two lesion candidate regions are on the same axial section, the display control function 154 allows marks such as squares to be displayed at corresponding positions in the MPR image of the axial section at the upper left of FIG. 3.

Furthermore, the display control function 154 allows marks to be displayed at the positions of the designated two lesion candidate regions in the volume rendering image. Note that, in the case of the Slab MIP image, the generation function 152 can regenerate the Slab MIP image by changing the Slab thickness such that two lesion candidate regions are included, and the display control function 154 can allow marks to be displayed at the positions of the designated two lesion candidate regions.

As described above, in the medical information processing apparatus 100, grouped AI analysis results and medical images corresponding to the analysis results are displayed on the same display screen. In the medical information processing apparatus 100, by receiving a change in the extraction condition, it is possible to change a group in which the analysis results are collectively collected. For example, as illustrated in FIG. 3, the display control function 154 allows a pull-down 21 to be displayed. The input interface 130 receives a change in the extraction condition by receiving an operation of the pull-down 21.

In the medical information processing apparatus 100 according to the present embodiment, grouping can be performed for each disease or certainty factor, in addition to the type of the learned model described above. For example, the extraction function 153 extracts output data related to each disease. As described above, the AI service server 200 includes a plurality of learned models and provides APIs for various image processing algorithms. A plurality of analysis results output by the learned models are related to various diseases, and a radiologist or a doctor in charge can make a diagnosis by referring to the analysis results.

For example, in diagnosis of cerebral infarction, when determining ischemia in the brain, it is useful to refer to analysis results of an algorithm for detecting a characteristic region from a difference in luminance values, analysis results of an algorithm for detecting a region indicating a characteristic perfusion state from a perfusion image, analysis results of an algorithm for detecting a region indicating a characteristic shape in the shape of a blood vessel, and the like, for medical image data of the brain.

Furthermore, for example, in diagnosis of myocardial infarction, it is useful to refer to analysis results of an algorithm for detecting a calcium score, analysis results of an algorithm for detecting blood flow, and the like, for medical image data of the heart. Furthermore, in diagnosis of valvular disease of the heart, it is useful to refer to analysis results of an algorithm for detecting a calcium score, analysis results of an algorithm for detecting a valve movement, and the like, for medical image data of the heart.

As described above, when diagnosing each disease, a radiologist or a doctor in charge can further improve the accuracy of diagnosis by comprehensively referring to the analysis results. In this regard, the extraction function 153 according to the present embodiment extracts analysis results of an algorithm related to a designated disease from the analysis results received from the AI service server 200. The display control function 154 performs control to display the analysis results for each disease.

FIG. 4A is a diagram illustrating an example of a group of analysis results according to the first embodiment. For example, as illustrated in FIG. 4A, the extraction function 153 extracts "algorithm A", "algorithm B", and "algorithm D" of a learned model related to "disease: XXXX". As illustrated in FIG. 4A, the display control function 154 allows thumbnail images and analysis results including analysis information of lesion candidate regions to be displayed in the display region R2 with respect to the extracted "algorithm A", "algorithm B", and "algorithm D".

Note that, when extracting analysis results related to a designated disease, for example, as indicated in the analysis result of "algorithm D", the lesion candidate regions are not necessarily detected. A radiologist or a doctor in charge refers to these results and makes a diagnosis related to "disease: XXXX".

Furthermore, for example, the extraction function 153 estimates a related disease based on a plurality of analysis results and extracts related analysis results for each estimated disease. That is, the extraction function 153 refers to the analysis results received from the AI service server 200, estimates a highly suspected disease, and extracts analysis results related to the estimated disease.

FIG. 4B is a diagram illustrating an example of a group of analysis results according to the first embodiment. For example, as illustrated in FIG. 4B, when lesion candidate regions are detected in "algorithm A", "algorithm C", and "algorithm E", the extraction function 153 estimates "lesion: XXXX" related to "algorithm A", "algorithm C", and "algorithm E" as "candidate disease". Then, the extraction function 153 extracts analysis results related to "candidate disease: XXXX". The display control function 154 performs control to display the extracted analysis results for each disease. Although FIG. 4B illustrates the analysis results of only "algorithm A", "algorithm C", and "algorithm E", when there is another algorithm related to "candidate disease: XXXX", the analysis results of the algorithm are extracted and displayed in the display region R2.

As an example of the extraction of the analysis results described above, in the analysis results for the medical image data of the heart, when the analysis results of the algorithm for detecting a calcium score include detection results of a region having a high calcium score, the analysis results of the algorithm for detecting a valve movement include detection results of a region indicating an abnormal movement, and no abnormal region is detected in the analysis results of the algorithm for detecting blood flow, the extraction function 153 determines that the possibility of valvular disease of the heart is high and extracts analysis results of an algorithm related to the valvular disease.

As described above, the extraction function 153 can extract analysis results based on various extraction conditions. Then, the display control function 154 allows the analysis results extracted by the extraction function 153 to be displayed together with medical images. When a plurality of groups are extracted, the display control function 154 can allow the groups to be displayed in an arbitrary order. For example, as illustrated in FIG. 3, when analysis results are extracted for a plurality of algorithms or when groups of analysis results are extracted for a plurality of diseases, the display control function 154 can allow the groups to be displayed, for example, from the top in descending order of certainty factor of the analysis results.

Furthermore, when there are past analysis results similar to the current analysis results, the display control function 154 can acquire the past analysis results and allow the current analysis results to be displayed in parallel. That is, the display control function 154 acquires a plurality of analysis results from a plurality of learned models in which past medical image data collected for the same part as that in medical image data is used as input data, and performs control to display analysis results based on the past medical image data corresponding to the analysis results based on the medical image data on the same screen.

Figure 5A:
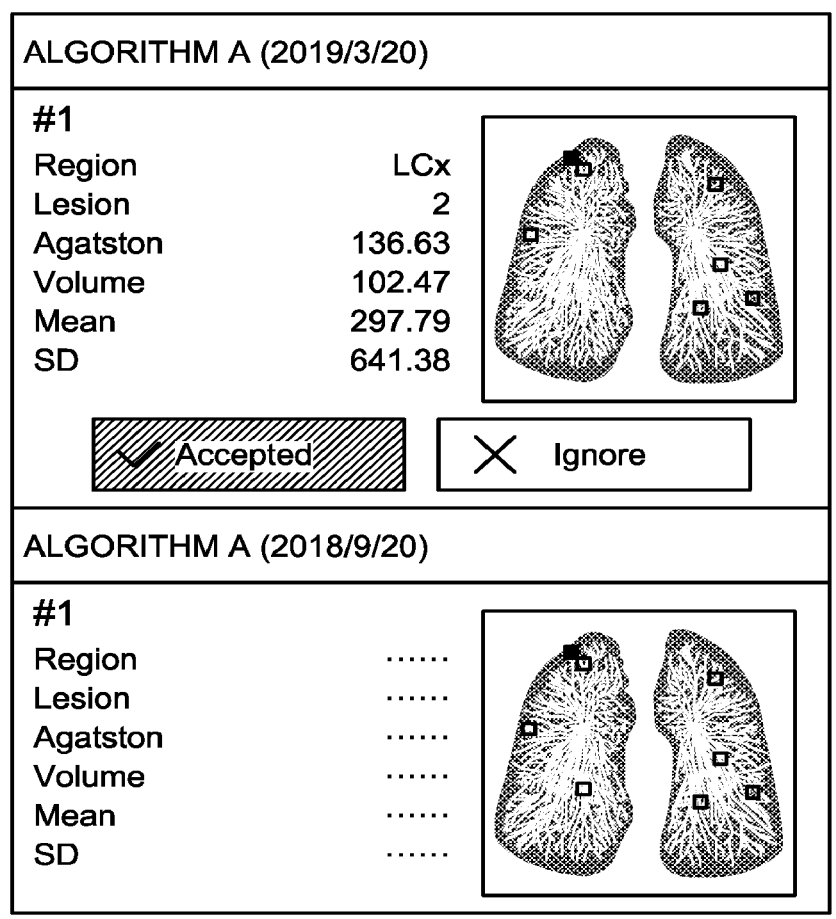
FIG. 5A is a diagram illustrating an example of parallel display by the display control function according to the first embodiment.

FIG. 5A is a diagram illustrating an example of parallel display by the display control function 154 according to the first embodiment. For example, as illustrated in FIG. 5A, the display control function 154 can allow the analysis result "algorithm A (Mar. 20, 2019)" extracted this time and the past analysis result "algorithm A (Sep. 20, 2018)" of the same algorithm to be displayed in parallel. When the past image is displayed, the display control function 154 performs the parallel display after aligning of a display image of the current analysis result and a display image of the past analysis result. That is, the display control function 154 allows the current image and the past image indicating the same position of a subject to be displayed.

The target past analysis results are all analysis results obtained by applying the same algorithm to the same image data of the same part of the same subject, but a target period may be set. For example, analysis results acquired in one year may be set as a target.

Furthermore, for example, the target past analysis results may be only analysis results approved by a radiologist or a doctor in charge. That is, the display control function 154 acquires only approved analysis results among the past analysis results similar to the current analysis results, and allows the acquired past analysis results to be displayed in parallel with the current analysis results.

Furthermore, for example, the target past analysis results may be similar analysis results without being limited to the same algorithm. For example, when there are two algorithms for detecting a pulmonary nodule, the display control function 154 may acquire analysis results of one of the algorithms as the past analysis results of the analysis results of the other.

Figure 5B:
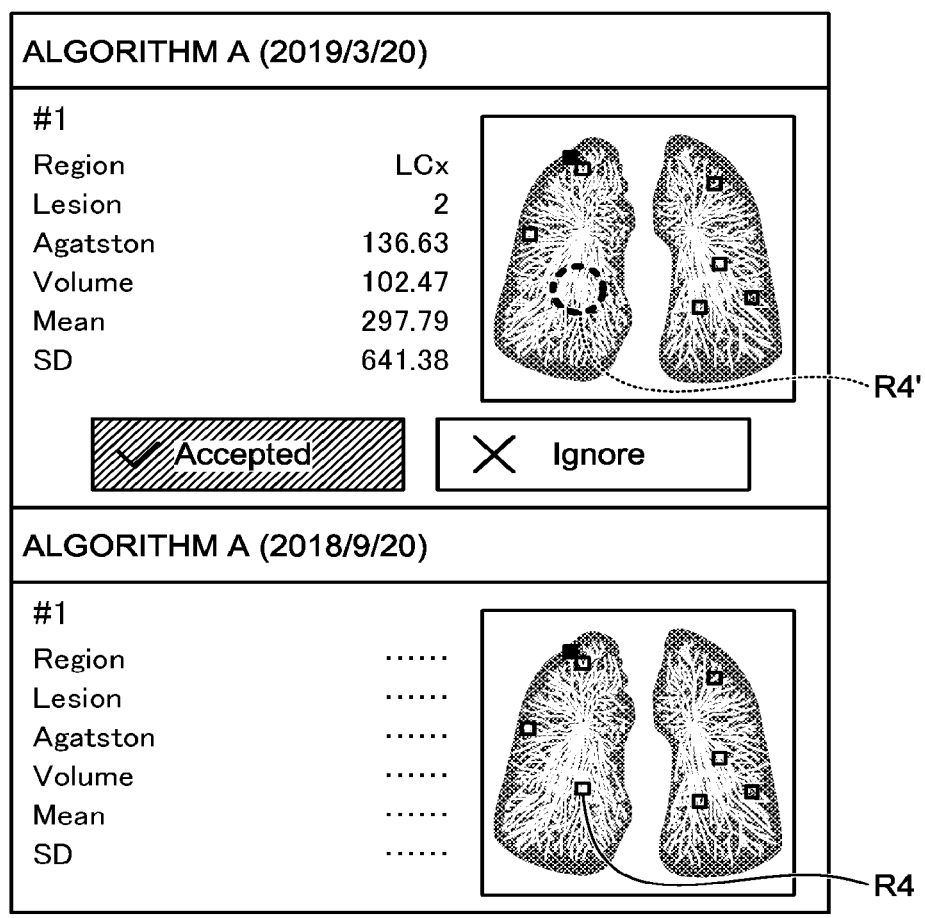
FIG. 5B is a diagram illustrating an example of parallel display by the display control function according to the first embodiment.

Furthermore, when the past analysis result is displayed in parallel, the display control function 154 can extract and display a difference. That is, the display control function 154 performs control to extract and display a difference between the analysis result based on medical image data and the analysis result based on the past medical image data. FIG. 5B is a diagram illustrating an example of parallel display by the display control function according to the first embodiment. For example, as illustrated in FIG. 5B, when a lesion candidate region R4 detected in the past analysis result has not been detected in the current analysis result, the display control function 154 allows a mark R4', which indicates that the lesion candidate region was detected in the past analysis result, to be displayed at a corresponding position on a thumbnail image in the current analysis result.

By observing the region of the mark R4', a radiologist or a doctor in charge can verify whether the reason that the lesion candidate region R4 detected in the past analysis result has not been detected in the current analysis result is a detection error by the learned model or whether the lesion has been cured.

Furthermore, the display control function 154 can allow a medical image to be displayed according to at least one of the type of medical image data, the part of the medical image data, and the type of analysis results. For example, when the medical image data is three-dimensional data, the display control function 154 allows a three-dimensional medical image such as a volume rendering image to be displayed as illustrated in the lower right of FIG. 3. Furthermore, for example, the display control function 154 can allow a medical image that is easy to observe to be displayed according to a part in the medical image data.

Figure 6:
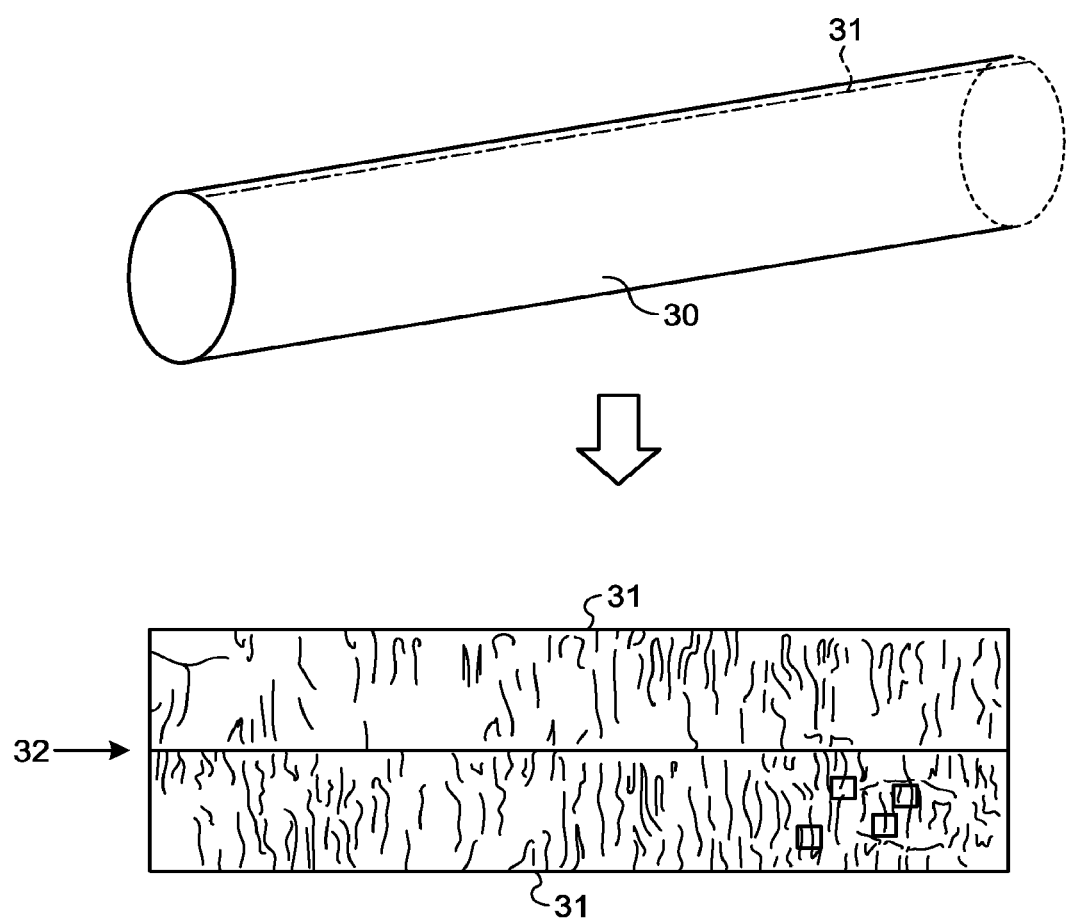
FIG. 6 is diagram illustrating an example of a medical image displayed by the display control function according to the first embodiment.

FIG. 6 is diagram illustrating an example of a medical image displayed by the display control function 154 according to the first embodiment. FIG. 6 illustrates a medical image displayed when a part of the medical image is the large intestine. Furthermore, in FIG. 6, the upper part indicates the large intestine before development and the lower part indicates a developed image in which the large intestine has been developed. For example, when the part is the large intestine, as illustrated in FIG. 6, the generation function 152 cuts a large intestine 30 along a cutting line 31 and generates the developed image in which the large intestine 30 has been developed around a development axis 32. The display control function 154 allows the developed image generated by the generation function 152 to be displayed in the display region R1.

Furthermore, for example, the display control function 154 can allow a medical image that is easy to observe to be displayed according to a disease based on analysis results. For example, when an abnormality is detected in analysis results related to valvular disease, the generation function 152 generates a medical image obtained by depicting a target valve from a direction parallel to the surface of the valve. The display control function 154 allows the medical image generated by the generation function 152 to be displayed in the display region R1.

Figure 7:
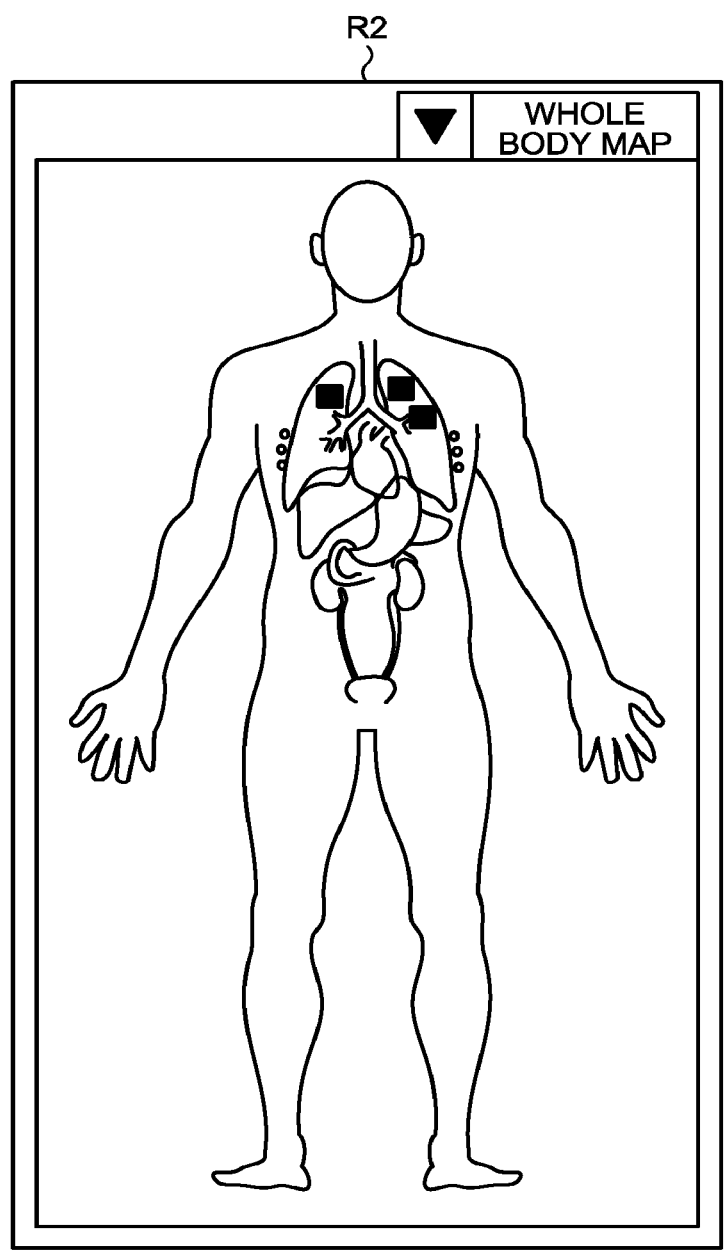
FIG. 7 is a diagram illustrating an example of display by the display control function according to the first embodiment.

Furthermore, when a plurality of analysis results are acquired for medical image data over a wide range of a subject, the display control function 154 can perform control to display a human body map indicating the analysis results. FIG. 7 is a diagram illustrating an example of display by the display control function 154 according to the first embodiment. For example, as illustrated in FIG. 7, when analysis results are acquired for medical image data over a wide range of a subject, the display control function 154 allows a whole body map in which marks are drawn at positions where an abnormality has been detected (positions of the lung in the drawing) to be displayed. In this way, a radiologist or a doctor in charge can grasp at a glance positions to be observed with more attention, thereby improving the efficiency of confirming a medical image.

As described above, in the medical information processing apparatus 100, the AI analysis results are grouped and displayed in the display region and corresponding medical images are displayed on the same screen to reduce the burden on a radiologist or a doctor in charge and to improve diagnosis efficiency, so that it is possible to improve the usefulness in the AI diagnosis support.

In the medical information processing apparatus 100, results approved by a radiologist or a doctor in charge can be reflected in external information. Specifically, the control function 151 reflects information, for which an approval operation has been received, in the external information. For example, the control function 151 reflects the information, for which the approval operation has been received, as at least one of a medical report, a work list, a notification to a doctor, and learning data of a learned model.

FIG. 8 is a diagram for explaining the process of the control function 151 according to the first embodiment. For example, when approved results are reflected in the work list, the control function 151 updates "Status" to "Completed (3)" as illustrated in "No. 4" of FIG. 8. Here, "3" in parentheses in "Status" indicates the number of approvals. That is, the control function 151 updates "Status" to the status indicating that the confirmation of medical image data of a subject of "No. 4" has been completed and three analysis results have been approved.

Furthermore, for example, the control function 151 perform control to transfer the analysis results, for which the approval operation has been received, to a medical report of a corresponding subject. As an example, the control function 151 automatically transfers, to the medical report, a medical image indicating a lesion candidate region for which the approval operation has been received, and analysis information including the size and the like of the lesion candidate region.

Furthermore, for example, when the input interface 130 receives the approval operation, the control function 151 transmits an e-mail and the like to a doctor in charge, thereby notifying that the lesion candidate region has been found and has been approved. In this way, for example, it is possible to quickly notify a doctor in charge of a diagnosis result even in an emergency.

Furthermore, for example, the control function 151 transmits the analysis results, for which the approval operation has been received, to the AI service server 200 as learning data of an algorithm. In this way, it is possible to automatically collect the learning data. Furthermore, for example, a new lesion candidate region is detected by comparison with past analysis results and approved analysis results are used as learning data, so that it is possible to construct a learned model for early detection of a lesion.

So far, each processing function included in the processing circuitry 150 of the medical information processing apparatus 100 has been described. When the processing circuitry 150 is implemented by a processor, each processing function included in the processing circuitry 150 is stored in the memory 120 in the form of a computer program executable by a computer. Then, the processing circuitry 150 reads and executes each computer program from the memory 120, thereby implementing a function corresponding to each computer program. In other words, the processing circuitry 150 having read each computer program has each function indicated in the processing circuitry 150 of FIG. 1. Although FIG. 1 illustrates that each processing function is implemented by a single processor, a plurality of independent processors may be combined to constitute a processing circuit and each processor may implement the function by executing the computer program. Furthermore, the processing functions included in the processing circuitry 150 may be implemented by being appropriately distributed or integrated in a single processing circuit or a plurality of processing circuits. Furthermore, in the example illustrated in FIG. 1, the single memory 120 has been described as storing therein the computer program corresponding to each processing function; however, it may be possible to employ a configuration in which a plurality of memories are arranged in a distributed manner and the processing circuit reads a corresponding computer program from an individual memory.

Figure 9:
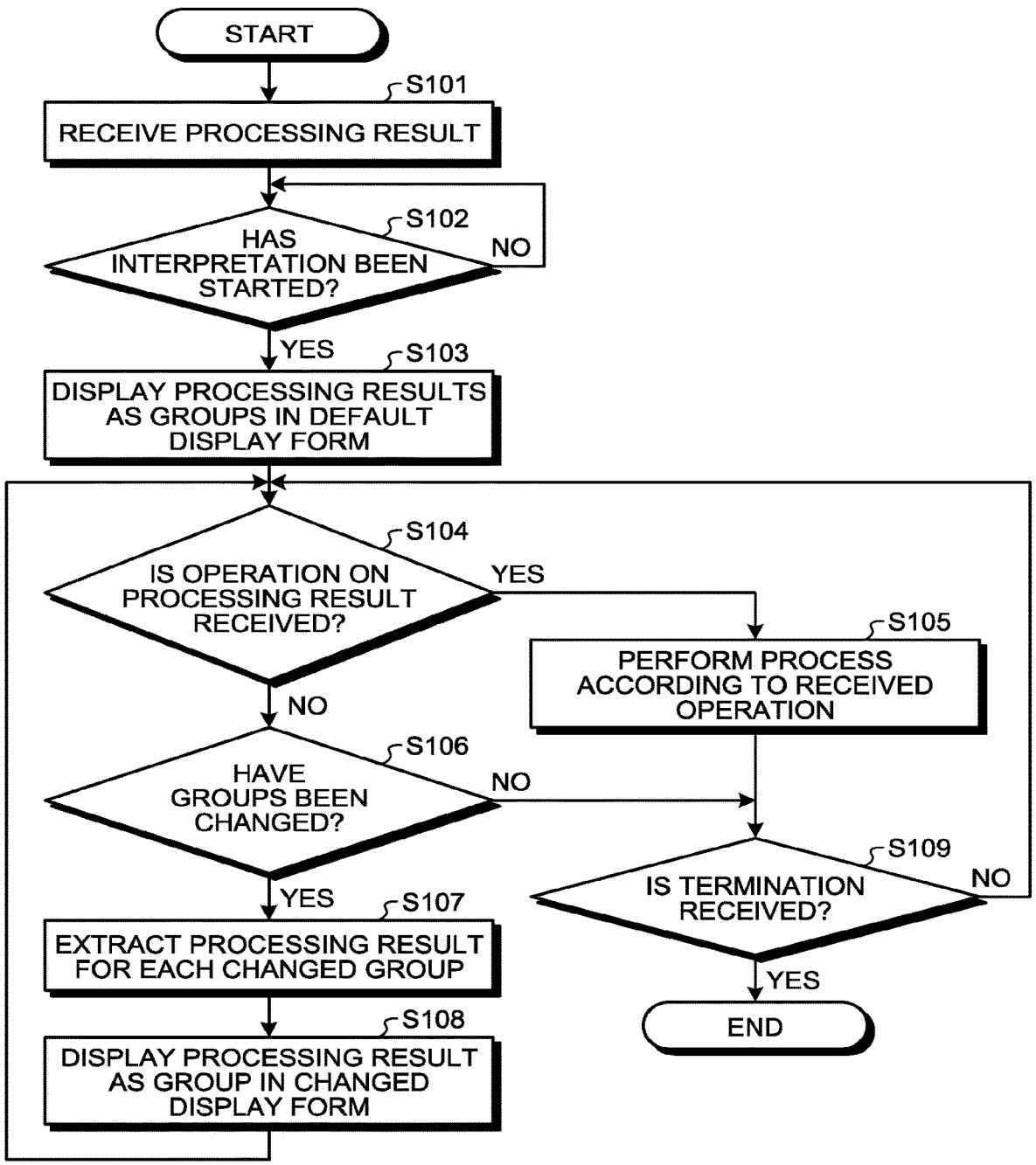
FIG. 9 is a flowchart illustrating a processing procedure by a medical information processing apparatus 100 according to the first embodiment.

Next, a processing procedure by the medical information processing apparatus 100 will be described. FIG. 9 is a flowchart illustrating the processing procedure by the medical information processing apparatus 100 according to the first embodiment. Steps S101, S102, and S109 in FIG. 9 are implemented by the processing circuitry 150 that calls from the memory 120 and executes a computer program corresponding to the control function 151. Furthermore, step S103 in FIG. 9 is implemented by the processing circuitry 150 that calls from the memory 120 and executes computer programs corresponding to the extraction function 153 and the display control function 154. Furthermore, steps S104 and S106 in FIG. 9 are implemented by the input interface 130. Furthermore, step S105 in FIG. 9 is implemented by the processing circuitry 150 that calls from the memory 120 and executes computer programs corresponding to the generation function 152 and the display control function 154. Furthermore, step S107 in FIG. 9 is implemented by the processing circuitry 150 that calls from the memory 120 and executes a computer program corresponding to the extraction function 153. Furthermore, step S108 in FIG. 9 is implemented by the processing circuitry 150 that calls from the memory 120 and executes a computer program corresponding to the display control function 154.

As illustrated in FIG. 9, in the medical information processing apparatus 100, the processing circuitry 150 first receives a plurality of processing results from the AI service server 200 (step S101) and determines whether interpretation has been started (step S102). When the interpretation is started (Yes at step S102), the processing circuitry 150 displays the processing results as groups in a default display form (step S103). For example, the processing circuitry 150 extracts an analysis result for each algorithm and allows the analysis result to be displayed for each algorithm.

Then, when the input interface 130 receives an operation on the processing result (step S104), the processing circuitry 150 performs a process according to the received operation (step S105). For example, when a lesion candidate region is designated, the processing circuitry 150 generates a corresponding medical image and allows the generated medical image to be displayed. Furthermore, for example, when the lesion candidate region is approved, the processing circuitry 150 reflects the approved lesion candidate region in external information.

On the other hand, when the input interface 130 receives no operation on the processing result (step S104), the processing circuitry 150 further determines whether the groups have been changed (step S106). When the groups have been changed (Yes at step S106), the processing circuitry 150 extracts a processing result for each changed group (step S107), and displays the processing result as a group in the changed display form (step S108).

After step S105 and when a negative determination is made in step S106, the processing circuitry 150 determines whether to terminate the interpretation (step S109). When the termination is not received (No at step S109), the determination process at step S104 is continued. On the other hand, when the termination is received (Yes at step S109), the medical information processing apparatus 100 terminates the processing procedure.

As described above, according to the first embodiment, the control function 151 acquires a plurality of pieces of output data respectively output from a plurality of analysis processes to which medical image data is input as input data. The extraction function 153 selectively extracts, from the pieces of output data, a plurality of pieces of output data based on an extraction condition. The display control function 154 performs control to display a plurality of pieces of information corresponding to the pieces of output data extracted by the extraction function 153 and a medical image related to any one piece of the information and generated from the medical image data. Consequently, in the medical information processing apparatus 100 according to the first embodiment, it is possible to display AI analysis results in an easy-to-view form, improve the efficiency of confirming the analysis results, and improve the usefulness in diagnosis support.

Furthermore, according to the first embodiment, the analysis results each include a thumbnail image on which an analysis result of the analysis process has been reflected and analysis information on the analysis result. The display control function 154 performs control to display medical images related to analysis results selected from the analysis results in parallel with the analysis results. Consequently, with the medical information processing apparatus 100 according to the first embodiment, it is possible to confirm the medical images related to the analysis results on the same display screen, and improve the efficiency of confirming the analysis results.

Furthermore, according to the first embodiment, the analysis results each include a thumbnail image indicating the position of an analysis result detected by the analysis process and analysis information on the position of the analysis result. The display control function 154 performs control to display a medical image corresponding to the position of the analysis result in information selected from the analysis results in parallel with the analysis results. Consequently, with the medical information processing apparatus 100 according to the first embodiment, it is possible to display analysis results that are easy to confirm.

Furthermore, according to the first embodiment, the extraction function 153 extracts the output data for each type of the analysis processes. The display control function 154 performs control to display a plurality of analysis results corresponding to the pieces of output data for each type of the analysis processes. Consequently, with the medical information processing apparatus 100 according to the first embodiment, it is possible to easily confirm the result for each analysis process.

Furthermore, according to the first embodiment, the extraction function 153 extracts output data related to each disease. The display control function 154 performs control to display the pieces of output data for each disease. Consequently, with the medical information processing apparatus 100 according to the first embodiment, it is possible to easily confirm comprehensive analysis results for a disease of interest.

Furthermore, according to the first embodiment, the extraction function 153 estimates related diseases based on results of the pieces of output data and extracts related output data for each estimated disease. The display control function 154 performs control to display the pieces of output data for each disease. Consequently, with the medical information processing apparatus 100 according to the first embodiment, it is possible to automatically display analysis results related to a highly suspected disease, thereby further improving confirmation efficiency.

Furthermore, according to the first embodiment, the input interface 130 receives an operation for changing the extraction condition. Consequently, with the medical information processing apparatus 100 according to the first embodiment, it is possible to easily perform desired grouping.

Furthermore, according to the first embodiment, the display control function 154 acquires a plurality of pieces of output data from the plurality of analysis processes in which past medical image data collected for the same part as that in the medical image data is used as input data, and performs control to display analysis results based on the past medical image data corresponding to the analysis results based on the medical image data in parallel. Consequently, with the medical information processing apparatus 100 according to the first embodiment, it is possible to enable easy comparison with the past information.

Furthermore, according to the first embodiment, the display control function 154 performs control to extract and display a difference between the analysis result based on the medical image data and the analysis result based on the past medical image data. Consequently, with the medical information processing apparatus 100 according to the first embodiment, it is possible to easily grasp a difference with the past results.

Furthermore, according to the first embodiment, the input interface 130 receives an approval operation for a plurality of analysis results corresponding to the pieces of output data extracted by the extraction function 153. The control function 151 reflects information, for which the approval operation has been received, in external information. Consequently, with the medical information processing apparatus 100 according to the first embodiment, it is possible to usefully use the approved information.

Furthermore, according to the first embodiment, the control function 151 reflects the information, for which the approval operation has been received, as at least one of a medical report, a work list, a notification to a doctor, and learning data for generating a learned model. Consequently, with the medical information processing apparatus 100 according to the first embodiment, it is possible to usefully use the approved information.

Furthermore, according to the first embodiment, the display control function 154 allows a medical image corresponding to at least one of the type of the medical image data, a part of the medical image data, and the type of the analysis results to be displayed. Consequently, with the medical information processing apparatus 100 according to the first embodiment, it is possible to automatically display a medical image required for observation and a medical image that is easy to observe.

Furthermore, according to the first embodiment, the display control function 154 performs control to display a human body map indicating the analysis results corresponding to the pieces of output data acquired by the control function 151. Consequently, with the medical information processing apparatus 100 according to the first embodiment, it is possible to grasp at a glance a region of interest.

Second Embodiment

So far, although the first embodiment has been described, various different embodiments other than the aforementioned first embodiment can be embodied.

The display example described in the aforementioned first embodiment is merely an example and may be displayed in various other forms. For example, the number of display images is not limited to four and may be three or less, or five or more.

Furthermore, in the aforementioned first embodiment, the case where the learned model generated by the machine learning is used as the analysis process to be used for the diagnosis support has been described as an example. However, the embodiment is not limited thereto and, for example, another analysis process such as computer-aided diagnosis (CAD) may be used. In such a case, for example, the control function 151 acquires results of a plurality of analysis processes by a plurality of applications. Then, the extraction function 153 groups the results of the analysis processes acquired by the control function 151. The display control function 154 performs control to display the grouped results of the analysis processes and medical images related to the results in parallel. Note that the analysis processes by the applications may be performed by an apparatus different from the medical information processing apparatus 100, or may be performed by the medical information processing apparatus 100.

Furthermore, in the aforementioned first embodiment, the case where the AI service server 200 includes a plurality of learned models and outputs output data according to the input of the medical image data (input data) has been described.

However, the embodiment is not limited thereto and, for example, the medical information processing apparatus 100 may include the learned models and output the output data according to the input of the medical image data (input data). In such a case, the extraction function 153 groups the results of the analysis processes output by the medical information processing apparatus 100.

Furthermore, in the aforementioned first embodiment, the case where the medical images and the results of the analysis processes (the thumbnail image, the analysis information, and the like) are displayed on the same screen has been described. However, the embodiment is not limited thereto and any display form may be used as long as it allows the medical images and the results of the analysis process to be displayed in parallel. For example, the display 140 may be configured by a plurality of displays, the medical images may be displayed on one of two displays arranged side by side, and the results of the analysis processes may be displayed on the other one of the two displays.

Furthermore, in the aforementioned first embodiment, the case where the current thumbnail image and the past thumbnail image are displayed on the same screen has been described. However, the embodiment is not limited thereto and any display form may be used as long as it allows the current thumbnail image and the past thumbnail image to be displayed in parallel. For example, the display 140 may be configured by a plurality of displays, the current thumbnail image may be displayed on one of two displays arranged side by side, and the past thumbnail image may be displayed on the other one of the two displays.

Furthermore, in the aforementioned first embodiment, the case where a group to be displayed is changed by receiving the operation of the pull-down 21 has been described. However, the embodiment is not limited thereto, and a tab may be provided for each extraction condition and the group to be displayed may be changed by selecting the tab. In such a case, the display control function 154 allows the display 140 to display a display screen including a tab indicating a label for identifying the extraction condition (group). Then, in response to a tab selection operation via the input interface 130, the display control function 154 allows analysis results and medical images of a group corresponding to a selected tab to be displayed. For example, the display control function 154 allows the display 140 to display a display screen including a tab indicating a label for identifying a group such as an algorithm, a disease, and a certainty factor, and to display the analysis results and the medical images to be displayed on the display screen according to the selection of the tab.

Furthermore, in the aforementioned first embodiment, the case where the work list is used for selecting a subject to be diagnosed next has been described. However, the embodiment is not limited thereto and the work list may be used for selecting a group to be displayed. In such a case, the display control function 154 allows the display 140 to display the work list including identification information for identifying a group, in addition to information on the subject. Then, in response to a selection operation on the identification information included in the work list, the display control function 154 allows the analysis results and the medical images of the group corresponding to the selected tab to be displayed on the display screen.

For example, the display control function 154 allows identification information for identifying a group, such as an algorithm, a disease, and a certainty factor, to be displayed in correlation with the information on the subject. Then, in response to the selection of the subject and the identification information, the display control function 154 allows the analysis results and the medical images of a corresponding group to be displayed on the display screen. For example, in the case of the display screen illustrated in FIG. 3, the display control function 154 regards the group selected by the work list as being selected by the pull-down 21, and allows corresponding analysis results and medical images to be displayed in the display regions, respectively. Furthermore, for example, in the case of a display screen including a tab indicating a label for identifying a group, the display control function 154 allows the display screen to be displayed in the state in which the tab of the group selected by the work list has been selected, thereby allowing the corresponding analysis results and medical images to be displayed.

Furthermore, in the aforementioned first embodiment, the case where the analysis results, for which the approval operation has been received, are transferred to the medical report of a corresponding subject has been described. However, the embodiment is not limited thereto and, for example, a report transfer button (GUI) may be provided and the analysis results may be transferred to the medical report of the corresponding subject according to the pressing of the report transfer button.

In such a case, the display control function 154 allows the report transfer button to be displayed on the display screen. The control function 151 reflects the analysis results, for which the approval operation is received, in the medical report at the timing at which the report transfer button has been pressed. For example, when the report transfer button is pressed every time the approval operation is performed, the control function 151 transfers the analysis results, for which the approval operation has been performed, to the medical report one by one. On the other hand, when the report transfer button is pressed after a plurality of approval operations are performed, the control function 151 collectively collects a plurality of analysis results corresponding to approval operations received until the report transfer button is pressed, and transfers the collected analysis results to the medical report.

Note that the term "processor" used in the above description, for example, means a circuit such as a central processing unit (CPU), a graphics processing unit (GPU), an application specific integrated circuit (ASIC), a programmable logic device (for example, a simple programmable logic device (SPLD)), a complex programmable logic device (CPLD), and a field programmable gate array (FPGA). The processor performs functions by reading and executing the computer programs stored in the memory 120.

Note that, instead of storing the computer programs in the memory 120, the computer programs may be directly incorporated in the circuit of the processor. In such a case, the processor performs the functions by reading and executing the computer programs incorporated in the circuit. Furthermore, the processor of the present embodiment is not limited to being configured as a single circuit and one processor may be configured by combining a plurality of independent circuits to perform functions thereof.

The computer program (medical information processing computer program) executed by the processor is provided by being incorporated in advance in a read-only memory (ROM), a storage circuit, and the like. Note that the computer program may be provided by being recorded on a computer readable storage medium, such as a CD (compact disc)-ROM, a flexible disk (FD), a CD-R (recordable), and a digital versatile disc (DVD), in a file format installable or executable in these devices. Furthermore, the computer program may be provided or distributed by being stored on a computer connected to a network such as the Internet and downloaded via the network. For example, the computer program is configured as a module including the aforementioned each functional unit. As actual hardware, the CPU reads and executes the computer program from the storage medium such as a ROM, so that each module is loaded on a main storage device and generated on the main storage device.

According to at least one embodiment described above, it is possible to improve the usefulness in diagnosis support.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
    a memory configured to store a plurality of analysis tools of different types, and store a table that associates the plurality of analysis tools with type information of each analysis tool;
    processing circuitry configured to
        acquire a plurality of pieces of output data by inputting a single piece of medical image data to each of the plurality of analysis tools,
        identify, based on the analysis tools to which the medical image data was input and the stored table, type information corresponding to each of the plurality of pieces of output data, respectively,
        classify the pieces of output data into a plurality of groups using the identified type information, and
        perform control to display a plurality of pieces of information corresponding to the pieces of classified output data in a display manner classified by group, and display a medical image related to any one piece of the information and generated from the single piece of medical image data; and
    an input interface configured to receive an approval operation for the plurality of pieces of information corresponding to the pieces of classified output data,
    wherein the displayed plurality of pieces of information each include a thumbnail image indicating a position of an analysis result detected by the plurality of analysis tools and analysis information of the position of the analysis result, and
    the processing circuitry is further configured to update at least one of a medical report, a work list, a notification to a doctor, and learning data for generating a learned model with those pieces of information for which the approval operation has been received, among the plurality of pieces of information.

2. The medical information processing apparatus according to claim 1, wherein the processing circuitry is further configured to perform control to display a related medical image related to information selected from the pieces of information in parallel with the pieces of information.

3. The medical information processing apparatus according to claim 2, wherein the processing circuitry is further configured to perform control to display a particular medical image corresponding to the position of the analysis result in information selected from the pieces of information to be displayed in parallel with the pieces of information.

4. The medical information processing apparatus according to claim 1, wherein the processing circuitry is further configured to perform control to display a plurality of pieces of information corresponding to the pieces of output data for each type of the analysis tools.

5. The medical information processing apparatus according to claim 1, wherein the processing circuitry is further configured to
    classify the pieces of output data into the plurality of groups according to diseases, and
    perform control to display the pieces of output data for each of the diseases.

6. The medical information processing apparatus according to claim 1, wherein the processing circuitry is further configured to
    estimate related diseases based on results of the pieces of output data,
    extract related output data for each estimated disease, and
    perform control to display the pieces of output data for each disease.

7. The medical information processing apparatus according to claim 1, wherein the input interface is further configured to change the type information of each analysis tool.

8. The medical information processing apparatus according to claim 1, wherein the processing circuitry is further configured to
    acquire a plurality of pieces of output data from the plurality of analysis tools in which past medical image data collected for a same part as a part in the single piece of medical image data is used as input data, and
    perform control to display information based on the past medical image data corresponding to the information based on the single piece of medical image data in parallel.

9. The medical information processing apparatus according to claim 8, wherein the processing circuitry is further configured to perform control to extract and display a difference between the information based on the single piece of medical image data and the information based on the past medical image data.

10. The medical information processing apparatus according to claim 1, wherein the processing circuitry is further configured to allow a medical image corresponding to at least one of a type of the single piece of medical image data, a part included in the single piece of medical image data, and a type of the information to be displayed.

11. The medical information processing apparatus according to claim 1, wherein the processing circuitry is further configured to perform control to display a human body map indicating the information corresponding to the pieces of acquired output data.

12. The medical information processing apparatus of claim 1, wherein the processing circuitry is further configured to input, as the input data to the plurality of analysis tools, a same image, being the single piece of medical image data.

13. A medical information processing method, comprising:

acquiring a plurality of pieces of output data by inputting a single piece of medical image data to each of a plurality of analysis tools stored by a memory configured to store the plurality of analysis tools of different types;

identifying, based on the analysis tools to which the medical image data was input and a stored table, type information corresponding to each of the plurality of pieces of output data respectively, the stored table being stored by the memory, the table associating the plurality of analysis tools with type information of each analysis tool;

classifying the pieces of output data into a plurality of groups using the identified type information;

performing control to display a plurality of pieces of information corresponding to the pieces of classified output data in a display manner classified by group, and display a medical image related to any one piece of the information and generated from the single piece of medical image data;

receiving an approval operation for the plurality of pieces of information corresponding to the pieces of classified output data; and updating at least one of a medical report, a work list, a notification to a doctor, and learning data for generating a learned model with those pieces of information for which the approval operation has been received, among the plurality of pieces of information, wherein the displayed plurality of pieces of information each include a thumbnail image indicating a position of an analysis result detected by the plurality of analysis tools and analysis information of the position of the analysis result.

* * * * *